United States Patent
Hamm

(10) Patent No.: US 6,395,951 B1
(45) Date of Patent: May 28, 2002

(54) ADSORPTIVE SEPARATION PRODUCT RECOVERY BY FRACTIONAL DISTILLATION

(75) Inventor: David A Hamm, Hinsdale, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/669,793

(22) Filed: Sep. 26, 2000

(51) Int. Cl.$^7$ .............................. C07C 7/12; B01D 3/00; C10G 7/00
(52) U.S. Cl. .................. 585/827; 585/820; 585/825; 585/828; 585/829; 585/830; 585/831; 208/347; 208/348; 208/349; 208/350; 208/355
(58) Field of Search ........................ 202/158; 203/42; 196/111; 585/820, 825, 827, 828–831; 208/347, 348, 349, 350, 355

(56) References Cited

U.S. PATENT DOCUMENTS

| | | |
|---|---|---|
| 2,471,134 A | 5/1949 | Wright |
| 3,201,491 A | 8/1965 | Stine et al. .................. 260/676 |
| 3,205,166 A | 9/1965 | Ludlow et al. .............. 208/310 |
| 3,510,423 A | 5/1970 | Neuzil et al. ................ 208/310 |
| 4,006,197 A | 2/1977 | Bieser .................. 260/676 MS |
| 4,036,745 A | 7/1977 | Broughton ................... 208/310 |
| 4,230,533 A | 10/1980 | Giroux ........................... 203/1 |
| 5,177,295 A | 1/1993 | Oroskar et al. ............. 585/805 |

OTHER PUBLICATIONS

Rudd, H. "Thermal Coupling for Energy Efficiency" *Supplement to The Chemical Engineer* p. s14–s15 Aug. 27, 1992.

*Primary Examiner*—Walter D. Griffin
*Assistant Examiner*—Tam M. Nguyen
(74) *Attorney, Agent, or Firm*—John G. Tolomei; John F. Spears, Jr.

(57) ABSTRACT

Construction and operational costs of recovering the extract or raffinate product of a simulated moving bed adsorptive separation process units are reduced by employing a dividing wall column to perform the separation. The raffinate or extract stream is passed into the column at an intermediate point on the first side of the dividing wall, with the column delivering the adsorptive separation product as a sidedraw from the opposite side of the dividing wall. A stream of co-adsorbed impurity is removed as an overhead stream and desorbent is recovered as a net bottoms stream.

10 Claims, 1 Drawing Sheet

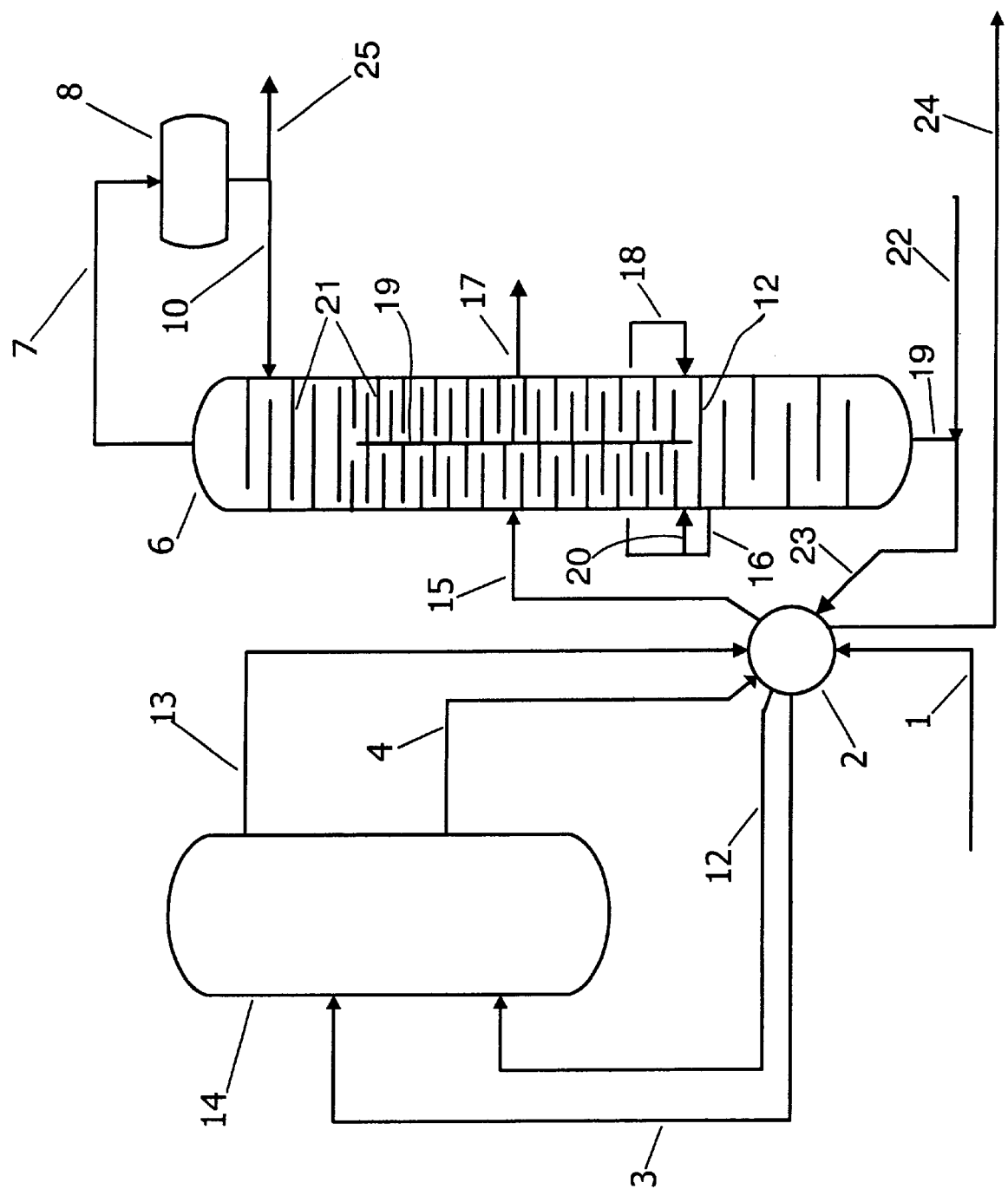

ADSORPTIVE SEPARATION PRODUCT RECOVERY BY FRACTIONAL DISTILLATION

FIELD OF THE INVENTION

The invention relates to a continuous adsorptive separation process used to separate chemical compounds such as $C_8$ aromatic hydrocarbons. The invention specifically relates to an innovative fractional distillation method which reduces the cost of recovering desorbent from the extract stream of a continuous adsorptive separation process.

BACKGROUND OF THE INVENTION

In many commercially important petrochemical and petroleum industry processes it is desired to separate closely boiling chemical compounds or to perform a separation of chemical compounds by structural class. It is very difficult or impossible to do this by conventional fractional distillation due to the requirement for numerous fractionation columns which may consume excessive amounts of energy. The relevant industries have responded to this problem by utilizing other separatory methods which are capable of performing a separation based upon chemical structure or characteristics. Adsorptive separation is one such method and is widely used to perform these separations.

In the practice of adsorptive separation a feed mixture comprising two or more compounds of different skeletal structure is passed through one or more beds of an adsorbent which selectively adsorbs a compound of one skeletal structure while permitting other components of the feed stream to pass through the adsorption zone in an unchanged condition. The flow of the feed through the adsorbent bed is stopped and the adsorption zone is then flushed to remove nonadsorbed materials surrounding the adsorbent. Thereafter the desired compound is desorbed from the adsorbent by passing a desorbent stream through the adsorbent bed. The desorbent material is commonly also used to flush nonadsorbed materials from the void spaces around and within the adsorbent. This could be performed in a single large bed of adsorbent or in several parallel beds on a swing bed basis. However, it has been found that simulated moving bed adsorptive separation provides several advantages such as high purity and recovery. Therefore, many commercial scale petrochemical separations especially for specific paraffins and xylenes are performed using simulated countercurrent moving bed (SMB) technology.

The passage of the desorbent through the adsorbent dislodges the selectively retained compounds to produce an extract stream. The extract stream contains a mixture of desorbent and the desired compounds, with these materials being then separated by distillation in a column referred to as the extract column. If more than one compound is retained on the adsorbent and removed as part of the extract, then it is necessary to perform yet another fractionation in a finishing column. The subject invention is aimed at improving the economics of the fractionation employed in recovering the final desired compound from the extract stream.

RELATED ART

Several economic advantages are derived from the continuous, as compared to batch-wise, operation of a large scale adsorptive separation processes. Recognition of this has driven the development of simulated moving bed (SMB) adsorptive separation processes. These processes typically employ a rotary valve and a plurality of lines to simulate the countercurrent movement of an adsorbent bed through adsorption and desorption zones. This is depicted, for instance, in U.S. Pat. No. 3,205,166 to D. M. Ludlow, et al. and U.S. Pat. No. 3,201,491 to L. O. Stine et al.

U.S. Pat. No. 3,510,423 to R. W. Neuzil et al. provides a depiction of the customary manner of handling the raffinate and extract streams removed from an SMB process, with the desorbent being recovered, combined and recycled to the adsorption zone. U.S. Pat. No. 4,036,745 describes the use of dual desorbents with a single adsorption zone to provide a higher purity paraffin extract. U.S. Pat. No. 4,006,197 to H. J. Bieser extends this teaching on desorbent recycling to three component desorbent mixtures.

U.S. Pat. No. 5,177,295 issued to A. R. Oroskar et al describes the fractionation of a "heavy" desorbent used in the recovery of paraxylene from a mixture of aromatic hydrocarbons.

The dividing wall or Petyluk configuration for fractionation columns was initially introduced some 50 years ago by Petyluk et al. A recent commercialization of a fractionation column employing this technique prompted more recent investigations as described in the article appearing at page s14 of a *Supplement to The Chemical Engineer*, Aug. 27, 1992.

The use of dividing wall columns in the separation of hydrocarbons is also described in the patent literature. For instance, U.S. Pat. No. 2,471,134 issued to R. O. Wright describes the use of a dividing wall column in the separation of light hydrocarbons ranging from methane to butane. U.S. Pat. No. 4,230,533 issued to V. A. Giroux describes a control system for a dividing wall column and illustrates the use of the claimed invention in the separation of aromatics comprising benzene, toluene and orthoxylene.

BRIEF SUMMARY OF THE INVENTION

The invention is an improved simulated moving bed adsorptive separation process characterized by the use of an integrated fractional distillation column to separate a stream comprising two extract components plus the desorbent into three product streams in only a single fractionation column. That is, the three-component extract stream of the adsorptive separation zone is separated into three high purity process streams in a single dividing wall column. A portion of the column is divided by a vertical wall into parallel fractionation zones with one receiving the extract stream and the other delivering a product stream of the adsorptive separation zone. The desorbent is preferably rejected from the bottom portion of the column. A light product may be recovered overhead. This reduces the capital and operating costs of the required separation and thus of the adsorption process.

One broad embodiment of the invention may be characterized as a simulated moving bed adsorptive separation process which comprises passing a feed stream comprising a first, second and third chemical compounds into an adsorption zone comprising a bed of a selective adsorbent maintained at adsorption promoting conditions under which the first compound is selectively retained on a quantity of the selective adsorbent compared to the second compound, with the third compound having a boiling point sufficiently different from the first and second compounds to allow its facile separation by fractional distillation and with the third compound being adsorbed onto the adsorbent to a lesser extent than said first chemical compound, and thus forming a raffinate stream comprising the second compound and a desorbent formerly present in the quantity of the selective adsorbent; passing a desorbent stream comprising a desorbent compound into contact with said quantity of the selective adsorbent, which has retained the first chemical compound, under desorption promoting conditions to yield an extract stream comprising the desorbent compound, the first compound and the third compound; passing the extract stream into a dividing wall fractionation column operated at fractionation conditions and divided into at least a first and a second parallel fractionation zones by a dividing wall, with the first and the second fractionation zones each having an upper and a lower end located within the fractionation column, with the first and second fractionation zones being in open communication at their upper ends with an undivided upper section of the fractionation column and in open communication at their lower ends with an undivided lower section of the fractionation column, and with the extract stream entering the column at an intermediate point of the first fractionation zone; removing an extract product stream comprising the first compound from an intermediate point of the second fractionation zone; recovering a product stream comprising the third compound from a first end of the fractionation column, removing a process stream comprising the desorbent compound from a second end of the fractionation column.

BRIEF DESCRIPTION OF THE DRAWING

The Drawing is a highly simplified process flow diagram showing the extract stream recovered from the adsorbent chamber 14 being passed into the left hand fractionation zone of a single dividing wall product recovery column 6.

PREFERRED EMBODIMENTS AND DETAILED DESCRIPTION

In many commercially important petrochemical and petroleum industry processes it is desired to separate closely boiling chemical compounds or to perform a separation of chemical compounds by structural class. Examples of this are the recovery of normal paraffins from petroleum kerosene fractions for use in the production of detergents and the recovery of paraxylene from a mixture of $C_8$ aromatics in the production of polyesters and other plastics. The separation of high octane hydrocarbons from a naphtha boiling range petroleum fraction and the recovery of olefins from a mixture of paraffins and olefins are other examples of situations in which the close volatility of the compounds or the overlap in boiling points across a broad boiling range of compounds makes the use of fractional distillation impractical. For instance in the case of the recovery of normal paraffins referred to above it is often desired to recover paraffins having a range of carbon numbers extending from about $C_9$ to $C_{12}$. This would require multiple fractional distillation columns. The resulting capital and operating costs makes this approach economically unattractive compared to adsorptive separation.

The relevant industries have responded to this problem by utilizing other separatory methods which are capable of performing a separation based upon chemical structure or characteristics. Adsorptive separation is such a method and is widely used to perform the separations mentioned above. In adsorptive separation one or more compounds are selectively retained upon an adsorbent and then released by the application of a driving force for the desorption step. In the subject process this driving force is provided by contacting the loaded adsorbent with a desorbent compound. Therefore the adsorbent must be continuously cycled between exposure to the feed stream and to a desorbent stream. As described below, this forms at least two effluent streams, the raffinate stream containing unadsorbed compounds and the extract stream containing the desired desorbent compound, which may comprise an admixture of several compounds, and the desorbent. It is an objective of the subject invention to provide a more economical process for recovering the desorbent compound from these two streams produced during adsorptive separation. It is a specific objective of the subject invention to provide an improved simulated moving bed adsorptive separation process having reduced capital costs. These objectives are achieved by reducing the number of fractionation columns required to recover the desorbent from the extract and desorbent. A single integrated column containing parallel fractionation zones in a single column is employed instead of individual columns. Each fractionation zone occupies only a portion of the cross-section of the column, and both zones are in open communication at both ends with a larger area undivided section of the column. This open communication at both the top or bottom end of the fractionation zones allows adaptation of the process to a desorbent having a lower or a higher boiling point than the raffinate and extract components of the feed.

The overall operation of the subject invention may be discerned by reference to the Drawing. The Drawing illustrates only a portion of a simulated moving bed adsorptive separation process having a single adsorbent chamber 14. Only one of the two columns employed in the process is shown. The other column may be of conventional design similar to the depicted column. For purposes of description it is assumed that the process is being employed to separate a feed stream of line 1 comprising a minor amount of toluene and a mixture of several $C_8$ aromatic hydrocarbons including paraxylene. The feed will normally also comprise metaxylene, orthoxylene and ethylbenzene. The toluene is a remnant of imprecise upstream fractionation. The very close volatilities of these $C_8$ aromatic compounds makes it impractical to separate them on a commercial scale by fractional distillation.

In the process depicted in the Drawing the feed stream of line 1 is passed into a rotary valve 2. This rotary valve has a number of ports corresponding to the number of adsorption chamber process streams plus the number of sub beds of adsorbent located in the one or more adsorbent chambers used in the process. As the adsorbent chamber(s) may contain from about 8 to about 24 adsorbent sub beds, there are a large number of bed lines involved in the process and about 12 to 30 separate lines normally connect to the rotary valve 2. For simplicity only those bed lines in use at the moment in time being depicted are shown on the drawing. The flows at other times are similar but occur via different bed lines not shown.

The rotary valve 2 directs the feed stream into bed line 3 which carries it to the adsorbent chamber 14. The feed stream enters into the adsorbent chamber at a boundary between two of the sub beds and is distributed across the cross-section of the chamber. It then flows downward through several sub-beds of adsorbent containing particles. The adsorbent selectively retains one compound or structural class of compound, which in this instance is paraxylene. The adsorbent also retains some toluene. The other $C_8$ components of the feed stream continue to flow downward and are removed from the adsorbent chamber in the raffinate stream carried by line 4. The raffinate stream will also comprise a varying amount of desorbent compound(s) flushed from the inter-particle void volume of the adsorbent by the flowing feed stream and also removed from the surface of the adsorbent. This desorbent is present in the bed prior to the adsorption step due to the prior performance of the desorption step. The raffinate stream enters the rotary valve 2 and is then directed by the valve into line 23. Line 23 carries the raffinate stream to a fractionation zone which is not shown in order to simplify the drawing. This may be a conventional or dividing wall column.

Simultaneous to the adsorption procedure a stream of desorbent is continuously passed into the adsorbent chamber 14 via line 12. The desorbent is distributed across the cross section of the column and moves downward through several beds of adsorbent which form a desorption zone. The desorbent removes paraxylene and toluene from the adsorbent. This creates a mixture of paraxylene, toluene and desorbent which flows through the section of the adsorbent chamber functioning as the desorption zone. This material is removed from the bottom of the chamber 14 and returned to the top of the chamber via a line not shown referred to in the art as the "pump around" line. This stream flows through more adsorbent at the top of the chamber forming the remainder of the desorption zone. It is then removed from the adsorbent chamber 14 via line 13 as the extract stream and passed into the rotary valve 2.

The rotary valve directs the extract stream of line 13 into line 15. Line 15 delivers the extract stream into a first vertical fractionation zone occupying a large portion of the left hand side of the mid section of the fractional distillation column 6. This fractionation zone contains about 30–50 fractionation trays 21 and is separated from a parallel second fractionation zone occupying the other half of the column cross-section by a substantially fluid tight vertical wall 19. The vertical wall is not necessarily centered in the column, and the two fractionation zones may differ in cross-sectional area or shape. The vertical wall 19 divides a large vertical portion of the column 6 into two parallel fractionation zones. The two zones are isolated from each other for the height of this wall, but communicate at the top and bottom ends. There is no direct vapor or liquid flow between the two fractionation zones through the dividing wall, but the upper end of the fractionation zone receiving the extract stream of line 15 is open to the internal volume of the column 6 containing an undivided fractionation zone having additional trays 21. Liquid may pass under the dividing wall 19 at the bottom of the two fractionation sections, although vapor flow is preferably restricted. Thus vapor and liquid can freely move around the wall between these two portions of the column. During operation, the extract stream is separated in the first fractionation zone, with the more volatile toluene moving upward out of the left hand first fractionation zone and emerging into the undivided upper portion of the column 6. As with the first fractionation zone, the upper end of the right hand second zone is in open communication with the upper section of the column 6, which contains additional fractionation trays 21 extending across the entire column cross-section.

The toluene present in the extract stream of line 15 is driven upward in the first fractionation zone and enters the top of the column 6. The top of the column is a purification zone which is designed to separate extract components from the toluene. This purification zone can also be used for a separation of different desorbent components when a multi-component desorbent stream is employed. A toluene-rich vapor stream is removed from the top of column 6 via line 7 and passed through an overhead condenser not shown to form liquid delivered to the receiver 8. A stream of liquid phase toluene is removed from the receiver and divided into a first portion which is returned to the top of the fractionation column 6 as reflux and a second portion which is removed from the process via line 25. As used herein the term "rich" is intended to indicate a concentration of the indicated compound or class of compounds greater than 50 and preferably greater than 75 mol percent.

The bottom of column 6 also comprises an undivided fractionation zone. This zone can receive liquid draining from both the first and second fractionation zones. This liquid is subjected to fractional distillation which drives $C_8$ aromatic hydrocarbons upwards as vapor while concentrating the less volatile desorbent into a bottoms liquid removed via line 19. This separation is effected through the use of a reboiler not shown providing vapor to the bottom undivided fractionation zone. The desorbent rich bottoms liquid is combined with a desorbent stream of line 22, which is obtained from the column receiving the raffinate of line 24. The recovered desorbent is then passed to the rotary valve 2 via line 23 for reuse in the process.

The undivided bottom section of the column 6 is depicted as separated from the two parallel fractionation zones by a gas flow control or gas trap out tray 12 located just bellow the bottom of wall 19. A slight gap at this point allows horizontal liquid flow between the parallel fractionation zones. This tray may have liquid sealed perforations allowing the normal downward flow of liquid, but its structure is such that the upward flow of vapor is at least greatly restricted. The tray may totally block the upward vapor flow. The use of this tray is preferred as it provides a means to positively control the division of the upward gas flow between the two fractionation zones, which is a prime means of controlling performance of the two zones. The total vapor flow is, therefore, preferably removed from the column via line 16 and divided between lines 18 and 20 which feed the vapor to the bottom of the two parallel fractionation zones. The gas flow may be controlled by one or more flow control valves or by adjusting the relative liquid levels in the bottom of the two zones. This is described in some detail in previously cited U.S. Pat. No. 4,230,533 for a slightly different arrangement.

A preferred embodiment of the invention may, therefore, be characterized as a simulated moving bed adsorptive separation process for the separation of xylene isomers, which process comprises passing a feed stream comprising a para-xylene, meta-xylene and toluene into an adsorption zone comprising a bed of a selective adsorbent maintained at adsorption promoting conditions under which the para-xylene is selectively retained on the selective adsorbent, with toluene being also adsorbed onto the adsorbent to a lesser extent than para-xylene, and thus forming a raffinate stream comprising meta xylene; passing a desorbent into contact with said bed of the selective adsorbent, which has retained para-xylene and toluene under desorption promoting conditions to yield an extract stream comprising the desorbent compound, para-xylene and toluene; passing the extract stream into a dividing wall fractionation column operated at fractionation conditions and divided into at least a first and a second parallel fractionation zones by a dividing wall, with each fractionation zone having an upper and a lower end located within the fractionation column, with the first and second fractionation zones being in open communication at their upper ends with an undivided upper section of the fractionation column and in open communication at their lower ends with an undivided lower section of the fractionation column, and with the extract stream entering the column at an intermediate point of the first fractionation zone; removing an extract product stream which is rich in para-xylene from an intermediate point of the second fractionation zone; removing an overhead vapor stream comprising toluene from an upper first end of the fractionation column, removing a bottoms stream comprising the desorbent from a lower second end of the fractionation column.

A representative comparison of the separation of the Drawing based solely upon engineering design calculations, which for the conventional case have the benefit of comparison to many operating units, indicates that a conventional two-column system (extract column and finishing column) which contains a total of 110 trays could be replaced with a single dividing wall column containing a total of 100 trays. The trays of the base case include 50 in the extract column and 60 in the finishing column. The dividing wall column requires a total reboiling duty of 93 MMBTU/hr versus 110 MMBTU/hr for the conventional column pair. The dividing wall column requires a total condenser duty of 87 MMBTU/hr versus 109 for the standard two-column case. Other economies are derived from a reduction in control systems, piping, pumps and plot space.

Operating conditions for adsorption include, in general, a temperature range of from about 20 to about 250° C., with from about 60 to about 200° C. being preferred. Temperatures from 90° C. to 160° C. are highly preferred for the second adsorption zone. Adsorption conditions also preferably include a pressure sufficient to maintain the process fluids in liquid phase; which may be from about atmospheric to 600 psig. Desorption conditions generally include the same temperatures and pressure as used for adsorption conditions. It is generally preferred that an SMB process is operated with an A:F flow rate through the adsorption zone in the broad range of about 1:1 to 5:1.0 where A is the volume rate of "circulation" of selective pore volume in the adsorbent and F is the feed flow rate. The practice of the subject invention requires no significant variation in operating conditions, adsorbent or desorbent composition within the adsorbent chambers. That is the adsorbent preferably remains at the same temperature throughout the process.

Although much of the description herein is set in terms of use of the invention in an SMB process, the invention is believed applicable to other modes of performing adsorptive separation such as a swing bed system employing one or more separate beds of adsorbent. The real limit to the application of the process is that the process produces an extract or raffinate stream comprising three compounds which it is desired to separate by fractionation. Another variation in the performance of the process is the replacement of the rotary valve with a manifold system of valves. Such systems have been described in the art such as U.S. Pat. No. 4,434,051, and become more practical as the number of sub-beds of adsorbent decreases.

Yet another variation which departs from the depiction in the Drawing is the instance of a separation in which the desorbent has a lower boiling point than the raffinate and extract components. In this case the desorbent is removed from the top of the column. Both of the parallel fractionation zones would still be in communication with the larger cross section portion of the column from which the desorbent is withdrawn. The use of "heavy" desorbents, that is desorbents having higher boiling points than the raffinate or extract components of the feed, in the separation of paraxylene is described in U.S. Pat. Nos. 5,107,062; 5,057,643 and 5,012,038. The fractionation of a heavy desorbent from the extract and raffinate is shown in previously cited U.S. Pat. No. 5,177,295.

The success of a particular adsorptive separation is determined by many factors. Predominant in these factors are the composition of the adsorbent (stationary phase) and desorbent (mobile phase) employed in the process. The remaining factors are basically related to process conditions.

The subject process is not believed to be limited to use with any particular form of adsorbent. The adsorbents employed in the process preferably comprise a molecular sieve such as a type A, X or Y zeolite or silicalite. Silicalite is well described in the literature. It is disclosed and claimed in U.S. Pat. No. 4,061,724 issued to Grose et al. A more detailed description is found in the article, "Silicalite, A New Hydrophobic Crystalline Silica Molecular Sieve," *Nature*, Vol. 271, Feb. 9, 1978 which is incorporated herein by reference for its description and characterization of silicalite. Silicalite is a hydrophobic crystalline silica molecular sieve having intersecting bent-orthogonal channels formed with two cross-sectional geometries, 6 Å circular and 5.1–5.7 Å elliptical on the major axis. A wide number of adsorbents are known and a starting molecular sieve is often treated by ion exchange or steaming etc to adjust its adsorptive properties. Adsorbents based upon zeolites X and Y are described in more detail in U.S. Pat. Nos. 3,663,638; 3,626,020 and 3,997,620.

The active component of the adsorbents is normally used in the form of particle agglomerates having high physical strength and attrition resistance. The agglomerates contain the active adsorptive material dispersed in an amorphous, inorganic matrix or binder, having channels and cavities therein which enable fluid to access the adsorptive material. Methods for forming the crystalline powders into such agglomerates include the addition of an inorganic binder, generally a clay comprising a silicon dioxide and aluminum oxide, to a high purity adsorbent powder in a wet mixture. The binder aids in forming or agglomerating the crystalline particles. The blended clay-adsorbent mixture may be extruded into cylindrical pellets or formed into beads which are subsequently calcined in order to convert the clay to an amorphous binder of considerable mechanical strength. The adsorbent may also be bound into irregular shaped particles formed by spray drying or crushing of larger masses followed by size screening. The adsorbent particles may thus be in the form of extrudates, tablets, spheres or granules having a desired particle range, preferably from about 16 to about 60 mesh (Standard U.S. Mesh) (1.9 mm to 250 microns). Clays of the kaolin type, water permeable organic polymers or silica are generally used as binders.

The active molecular sieve component of the adsorbents will ordinarily be in the form of small crystals present in the adsorbent particles in amounts ranging from about 75 to about 98-wt. % of the particle based on volatile-free composition. Volatile-free compositions are generally determined after the adsorbent has been calcined at 900° C. in order to drive off all volatile matter. The remainder of the adsorbent will generally be the inorganic matrix of the binder present in intimate mixture with the small particles of the silicalite material. This matrix material may be an adjunct of the manufacturing process for the silicalite, for example, from the intentionally incomplete purification of the silicalite during its manufacture.

Those skilled in the art will appreciate that the performance of an adsorbent is often greatly influenced by a number of factors not related to its composition such as operating conditions, feed stream composition and the water content of the adsorbent. The optimum adsorbent composition and operating conditions for the process are therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500° C. under an inert gas purge such as nitrogen for a period of time sufficient to achieve a constant weight. For the subject process it is preferred that the water content of the adsorbent results in an LOI at 900° C. of less than 7.0% and preferably within the range of from 0 to 4.0 wt. %. As the process fluids may dry the adsorbent, the hydration level of the sieve is normally controlled by controlled water injection, as via the desorbent stream.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In adsorptive separation processes, which are generally operated continuously at substantially constant pressures and a temperature which insures liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost.

As indicated above, the desorbent may be a mixture of two or more compounds. For instance a preferred desorbent for the separation of normal $C_9$–$C_{11}$ paraffins from kerosene comprises a mixture of a normal paraffin and a cycloparaffin (naphthene). A mixture in which the normal and cycloparaffins have the same carbon number is highly preferred, with carbon numbers of the desorbent compounds being in the general range of 5 to 8. The preferred normal paraffin is n-hexane, and the desorbent may range from 0 to 100% normal paraffin. The desorbent may also be 100% cycloparaffin. The desorbents preferred for the separation of $C_8$ aromatic hydrocarbons differs from those preferred for paraffin separations. The preferred "light" desorbent, which is removed overhead in the subject process is toluene. A preferred heavy desorbent is para-diethylbenzene, which may be used in admixture with a saturated hydrocarbon. Other heavy desorbents for this separation include Indane and Indan derivatives, diethyltoluene and Tetralin derivatives as described in U.S. Pat. No. 5,107,062.

Further details on equipment and techniques for use in an SMB process may be found in U.S. Pat. Nos. 3,208,833; 3,214,247; 3,392,113; 3,455,815; 3,523,762; 3,617,504; 3,686,342; 4,006,197; 4,133,842; 4,434,051 and 5,177,295, which are incorporated herein by reference for this teaching. A different type of simulated moving bed operation which can be performed using similar equipment, adsorbent and conditions but which simulates cocurrent flow of the adsorbent and liquid in the adsorption chambers is described in U.S. Pat. Nos. 4,402,832 and 4,498,991.

A related SMB processing technique is the use of "zone flush." The zone flush forms a buffer zone between the feed and extract bed lines to keep the desorbent e.g. normal pentane, from entering the adsorption zone. While the use of a zone flush requires a more complicated, and thus more costly rotary valve, the use of zone flush is preferred in the adsorption zones when high purity extract product are desired. In practice, a quantity of the mixed component desorbent recovered overhead from the extract and/or raffinate columns is passed into a separate splitter column. A high purity stream of the lower strength component of the mixed component desorbent is recovered and used as the zone flush stream. Further information on the use of dual component desorbents and on techniques to improve product purity such as the use of flush streams may be obtained from U.S. Pat. Nos. 3,201,491; 3,274,099; 3,715,409; 4,006,197 and 4,036,745 which are incorporated herein by reference for their teaching on this aspect of SMB technology.

SMB Technology has been applied to a wide variety of chemicals in addition to those described above. For instance, U.S. Pat. No. 4,467,126 describes the recovery of a di-substituted benzene such as a nitrotoluene isomer. The separation of 2,6 di methyl naphthalene is described in U.S. Pat. No. 5,004,853 and 2,7 di isopopylnaphthalene in U.S. Pat. No. 5,012,039. SMB technology has been extended to the separation of sugars, to the separation of chiral compounds and to more complicated organics such as fatty acids and triglycerides as degsribed in U.S. Pat. No. 5,225,580. The separation of fatty acids is described in U.S. Pat. Nos. 4,404,145; 4,770,819; 5,171,870 and 5,179,219. It is believed the subject process can be applied to any such SMB process requiring desorbent recovery from extract or raffinate components, especially when a third component separable by fractionation is also present.

For purposes of this invention, various terms used herein are defined as follows. A "feed mixture" is a mixture containing one or more extract components and one or more raffinate components to be separated by the process. The term "feed stream" indicates a stream of a feed mixture which is passed into contact with the adsorbent used in the process. An "extract component" is a compound or class of compounds that is more selectively adsorbed by the adsorbent while a "raffinate component" is a compound or type of compound that is less selectively adsorbed. The term "desorbent material" shall mean generally a material capable of desorbing an extract component from the adsorbent. The term "raffinate stream" or "raffinate output stream" means a stream in which a raffinate component is removed from the adsorbent bed after the adsorption of extract compounds. The composition of the raffinate stream can vary from essentially 100% desorbent material to essentially 100% raffinate components. The term "extract stream" or "extract output stream" means a stream in which an extract material, which has been desorbed by a desorbent material, is removed from the adsorbent bed. The composition of the extract stream can vary from essentially 100% desorbent material to essentially 100% extract components. At least portions of the extract stream and the raffinate stream are passed to separation means, typically fractional distillation columns, where at least a portion of desorbent material is recovered and an extract product and a raffinate product are produced. The terms "extract product" and "raffinate product" mean streams produced by the process containing, respectively, an extract component and a raffinate component in higher concentrations than those found in the extract stream and the raffinate stream withdrawn from adsorbent chamber. The extract stream may be rich in the desired compound or may only contain an increased concentration.

It has become customary in the art to group the numerous beds in the SMB adsorption chamber(s) into a number of zones. Usually the process is described in terms of 4 or 5 zones. First contact between the feed stream and the adsorbent is made in Zone I, the adsorption zone. The adsorbent or stationary phase in Zone I becomes surrounded by liquid which contains the undesired isomer(s), that is, with raffinate. This liquid is removed from the adsorbent in Zone II, referred to as a purification zone. In the purification zone the undesired raffinate components are flushed from the void volume of the adsorbent bed by a material which is easily separated from the desired component by fractional distillation. In Zone III of the adsorbent chamber(s) the desired isomer is released from the adsorbent by exposing and flushing the adsorbent with the desorbent (mobile phase). The released desired component and accompanying desorbent are removed from the adsorbent in the form of the extract stream. Zone IV is a portion of the adsorbent located between Zones I and III which is used to segregate Zones I and III. In Zone IV desorbent is partially removed from the adsorbent by a flowing mixture of desorbent and undesired components of the feed stream. The liquid flow through Zone IV prevents contamination of Zone III by Zone I liquid by flow cocurrent to the simulated motion of the adsorbent from Zone III toward Zone I. A more thorough explanation of simulated moving bed processes is given in the Adsorptive Separation section of the Kirk-Othmer Encyclopedia of Chemical Technology at page 563. The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber.

What is claimed is:

1. A simulated moving bed adsorptive separation process which comprises:
   a.) passing a feed stream comprising a first, second and third chemical compounds into an adsorption zone comprising a bed of a selective adsorbent maintained at adsorption promoting conditions under which the first compound is selectively retained on a quantity of the selective adsorbent compared to the second compound, with the third compound having a boiling point sufficiently different from the first and second compounds to allow its facile separation by fractional distillation and with the third compound being adsorbed onto the adsorbent to a lesser extent than said first chemical compound, and thus forming a raffinate stream comprising the second compound and a desorbent formerly present in the quantity of the selective adsorbent;
   b.) passing a desorbent stream comprising the desorbent into contact with said quantity of the selective adsorbent, which has retained the first chemical compound, under desorption promoting conditions to yield an extract stream comprising the desorbent, the first compound and the third compound;
   c.) passing the extract stream into a dividing wall fractionation column operated at fractionation conditions and divided into at least a first and a second parallel fractionation zones by a dividing wall, with the first and the second fractionation zones each having an upper and a lower end located within the fractionation column, with the first and second fractionation zones being in open communication at their upper ends with an undivided upper section of the fractionation column and in open communication at their lower ends with an undivided lower section of the fractionation column, and with the extract stream entering the column at an intermediate point of the first fractionation zone;
   d.) removing an extract product stream comprising the first compound from an intermediate point of the second fractionation zone;
   e.) recovering a product stream comprising the third compound from a first end of the fractionation column,
   f.) removing a process stream comprising the desorbent from a second end of the fractionation column.

2. The process of claim 1 wherein the undivided upper section of the fractionation column is located in the upper third of the fractionation column, and the process stream comprising the desorbent is removed from the upper end of the fractionation column.

3. The process of claim 1 wherein the undivided lower section of the fractionation column is located in the lower third of the fractionation column, and the process stream comprising the desorbent compound is removed from the lower end of the fractionation column.

4. The process of claim 1 wherein the first and second chemical compounds are paraffinic hydrocarbons.

5. The process of claim 1 wherein the first and second chemical compounds are aromatic hydrocarbons.

6. A simulated moving bed adsorptive separation process which comprises:
   a.) passing a feed stream comprising a first, second and third chemical compounds into an adsorption zone comprising a bed of a selective adsorbent maintained at adsorption promoting conditions under which the first chemical compound is selectively retained on a quantity of the selective adsorbent, with the second compound having a lower boiling point than the first and third compounds and being adsorbed onto the adsorbent to a lesser extent than said first compound, and thereby forming a raffinate stream comprising the second compound and a desorbent compound formerly present in the quantity of the selective adsorbent;
   b.) passing a desorbent stream into contact with said quantity of the selective adsorbent, which has retained the first compound, under desorption promoting conditions to yield an extract stream comprising the desorbent compound, the first compound and the third compound;
   c.) passing the extract stream into a dividing wall fractionation column operated at fractionation conditions and divided into at least a first and a second parallel fractionation zones by a dividing wall, with the first and the second fractionation zones each having an upper and a lower end located within the fractionation column, with the first and second fractionation zones being in open communication at their upper ends with an undivided upper section of the fractionation column and in open communication at their lower ends with an undivided lower section of the fractionation column, and with the extract stream entering the column at an intermediate point of the first fractionation zone;

d.) removing an extract product stream from an intermediate point of the second fractionation zone;

e.) removing an overhead vapor stream comprising the third chemical compound from an upper first end of the fractionation column, f.) removing a bottoms stream comprising the desorbent compound from a lower second end of the fractionation column.

7. The process of claim 6 wherein the first chemical compound is a normal paraffin.

8. The process of claim 6 wherein the first chemical compound is an olefin.

9. A simulated moving bed adsorptive separation process for the separation of xylene isomers, which process comprises:

a.) passing a feed stream comprising a para-xylene, meta-xylene and toluene into an adsorption zone comprising a bed of a selective adsorbent maintained at adsorption promoting conditions under which the para-xylene is selectively retained on the selective adsorbent, with toluene being also adsorbed onto the adsorbent to a lesser extent than para-xylene, and thus forming a raffinate stream comprising meta xylene;

b.) passing a desorbent into contact with said bed of the selective adsorbent, which has retained para-xylene and toluene, under desorption promoting conditions to yield an extract stream comprising the desorbent, para-xylene and toluene;

c.) passing the extract stream into a dividing wall fractionation column operated at fractionation conditions and divided into at least a first and a second parallel fractionation zones by a dividing wall, with each fractionation zone having an upper and a lower end located within the fractionation column, with the first and second fractionation zones being in open communication at their upper ends with an undivided upper section of the fractionation column and in open communication at their lower ends with an undivided lower section of the fractionation column, and with the extract stream entering the column at an intermediate point of the first fractionation zone;

d.) removing an extract product stream which is rich in para-xylene from an intermediate point of the second fractionation zone;

e.) removing an overhead vapor stream comprising toluene from an upper first end of the fractionation column, f.) removing a bottoms stream comprising the desorbent from a lower second end of the fractionation column.

10. The process of claim 9 wherein the upward flow of vapor from the lower section of the fractionation column into the first and second fractionation zones is collected and then divided between the first and second fractionation zones in a controlled manner.

* * * * *